(12) United States Patent
Charbonneau

(10) Patent No.: US 6,451,206 B1
(45) Date of Patent: Sep. 17, 2002

(54) SYSTEM FOR CONVERTING ORGANIC WASTE RESERVOIRS ONTO ANAEROBIC DIGESTERS

(76) Inventor: Robert Charbonneau, 250, rue St-Sylvestre, porte 1, Longueuil Quebec (CA), J4H 2W4

( * ) Notice: Subject to any disclaimer, the term of this patent is extended or adjusted under 35 U.S.C. 154(b) by 0 days.

(21) Appl. No.: 09/756,135

(22) Filed: Jan. 9, 2001

(30) Foreign Application Priority Data

Dec. 12, 2000 (CA) ............................................. 2328015

(51) Int. Cl.$^7$ ................................................. C02F 3/28
(52) U.S. Cl. ...................... 210/170; 210/232; 210/603; 210/DIG. 9
(58) Field of Search ................................. 210/603, 612, 210/613, 747, 170, DIG. 9, 232; 435/289.1, 290.1; 48/127.3

(56) References Cited

U.S. PATENT DOCUMENTS

| | | | |
|---|---|---|---|
| 3,933,628 A | * | 1/1976 | Varani |
| 4,040,963 A | * | 8/1977 | Garrott, Jr. |
| 4,100,023 A | | 7/1978 | McDonald |
| 4,221,571 A | | 9/1980 | Rhoades |
| 4,274,838 A | * | 6/1981 | Dale et al. |
| 4,401,441 A | | 8/1983 | Chase |
| 4,437,987 A | * | 3/1984 | Thornton et al. |
| 4,551,243 A | | 11/1985 | Martin |
| 4,579,654 A | | 4/1986 | Bremmer |
| 4,622,147 A | | 11/1986 | Vellinga |
| 4,668,388 A | | 5/1987 | Dibble et al. |
| 4,750,454 A | | 6/1988 | Santina et al. |
| 5,238,844 A | * | 8/1993 | Wight et al. |
| 5,423,895 A | * | 6/1995 | Wight et al. |
| 5,505,848 A | | 4/1996 | Landine et al. |
| 5,863,434 A | | 1/1999 | Massé et al. |
| 6,247,278 B1 | * | 6/2001 | Rysgaard |
| 6,296,766 B1 | * | 10/2001 | Breckenridge |

* cited by examiner

Primary Examiner—David A. Simmons
Assistant Examiner—Fred Prince
(74) Attorney, Agent, or Firm—Ogilvy Renault; Michel Sofia

(57) ABSTRACT

The system for converting organic waste reservoirs into anaerobic digester comprises an inflatable roof structure adapted to be installed on a variety of reservoirs to seal it from the atmosphere. The roof structure includes an inner gas-impermeable membrane which is adapted to raise and lower with the level of organic waste contained in the reservoir. A peripheral fold is defined in the gas-impermeable membrane adjacent the inner surface of the surrounding wall of the reservoir to form a downwardly depending skirt which acts as a gas barrier to prevent gas leakage along the inner surface of the reservoir. A gas removal unit is also provided for removing biogas trapped beneath the gas-impermeable membrane from the reservoir.

42 Claims, 5 Drawing Sheets

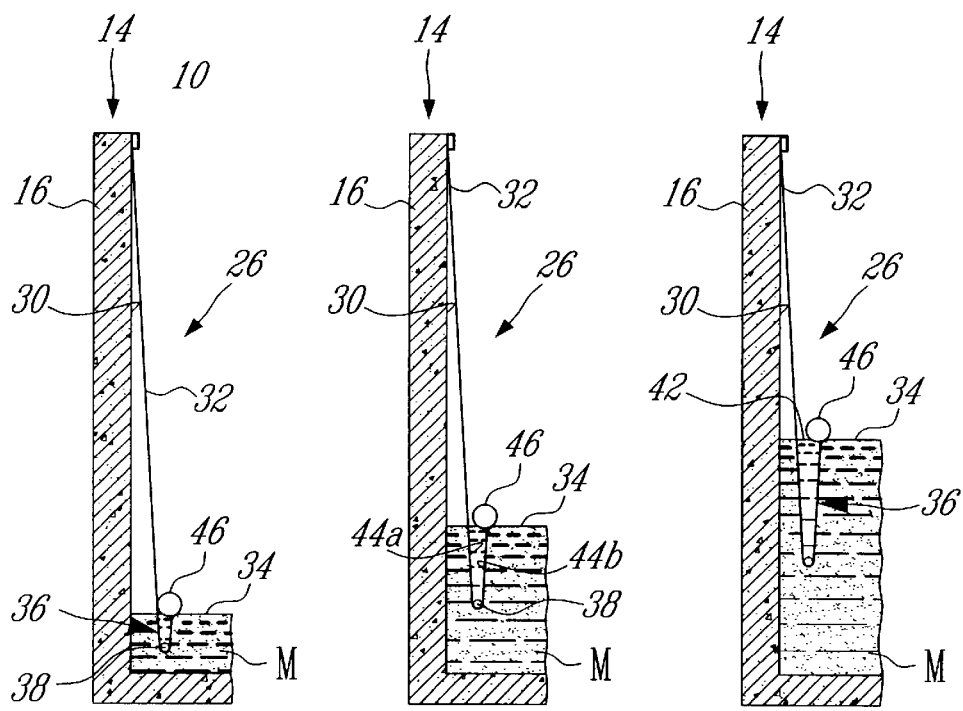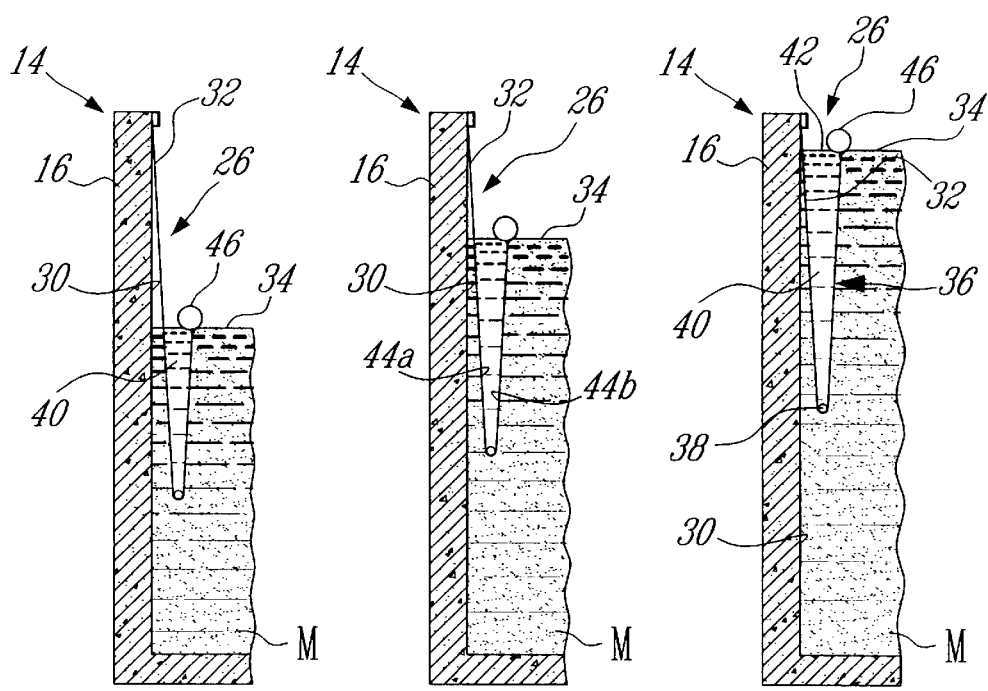

SYSTEM FOR CONVERTING ORGANIC WASTE RESERVOIRS ONTO ANAEROBIC DIGESTERS

BACKGROUND OF THE INVENTION

1. Field of the Invention

The present invention relates to organic waste treatment and, more particularly, to a system for converting organic waste reservoirs into anaerobic digesters.

2. Description of the Prior Art

Throughout the world where there is large hog livestock, the management of the hog manure is problematic. The hog manure is often stored and subsequently spread on fields as a fertilizer. However, raw manure is quite toxic and detrimental to the environment by polluting the air, the water and the soil. In order to overcome this problem, the raw hog manure must be treated. Accordingly, various treatment methods have been developed. One of these methods consists in promoting the action of certain types of bacteria contained in the hog manure so that these bacteria digest the organic matter in transforming the latter into an inert and deodorized fertilizer. The basic conditions of this digestion process are the absence of air and the obtention of an appropriate constant temperature. This process is characterized as anaerobic digestion and is at the root of the present invention.

The raw hog manure is typically stored within cylindrical concrete reservoirs. When such reservoirs are not covered, the precipitation, e.g. rain, are allowed to fall into the reservoirs, thereby increasing the volume of the manure and, thus, the cost associated with the transportation thereof. Furthermore, the presence of oxygen promotes the proliferation of a particular type of bacteria that produce carbonic gas ($CO_2$), which is associated with nauseating odors. Open reservoirs also permit the evaporation of the nitrogen contained in the raw manure, which significantly reduces the fertilizing potential thereof.

Reservoirs containing other types of organic waste also suffers from similar drawbacks. Accordingly, there is a need for a new system which could be adapted to a variety of organic waste reservoirs to convert the same into anaerobic digesters.

SUMMARY OF THE INVENTION

It is therefore an aim of the present invention to provide a new system for converting a reservoir into an anaerobic digester.

It is also an aim of the present invention to provide a new roof structure which is adapted to seal a reservoir from the atmosphere.

It is a further aim of the present invention to provide a new sealing system which is adapted to be installed on a reservoir to seal it from the atmosphere while allowing the recovery of the biogas generated during the anaerobic transformation of the organic waste contained in the reservoir.

Therefore, in accordance with the present invention, there is provided a system for converting a reservoir into an anaerobic digester in which organic waste contained in the reservoir can be at least partly anaerobically decomposed. The system comprises a roof structure adapted to be installed on the reservoir to seal the reservoir from the atmosphere. The roof structure includes a gas-impermeable membrane adapted to extend over the organic waste contained in the reservoir for trapping, beneath the gas-impermeable membrane, gas generated during decomposition of the organic waste in the reservoir. The gas-impermeable membrane has a peripheral depending skirt adapted to extend downwardly and inwardly of an inner surface of a surrounding containing wall of the reservoir below a level of organic waste to prevent the gas from escaping along the inner surface of the reservoir.

In accordance with a further general aspect of the present invention, there is provided an anaerobic digester comprising a surrounding wall forming a digester vessel for containing an organic waste material, and a roof structure for sealing the digester vessel from the atmosphere. The roof structure comprises a gas-impermeable membrane adapted to extend over the organic waste contained in said digester vessel for trapping, beneath said gas-impermeable membrane, gas generated from a decomposition of the organic waste. The gas-impermeable membrane has a peripheral depending skirt adapted to extend downwardly and inwardly of an inner surface of the surrounding wall of the digester vessel below a level of organic waste to prevent the gas from escaping along the inner surface.

In accordance with a further general aspect of the present invention, there is provided a system for converting an existing reservoir containing an organic waste into an anaerobic digester, comprising an inflatable roof structure adapted to be installed on the existing reservoir for allowing anaerobic conditions to be reached therein, and a gas removal unit for removing gas captured beneath said inflatable roof structure from the existing reservoir.

In accordance with a still further general aspect of the present invention, there is provided a system for converting a reservoir containing organic waste into an anaerobic digester, comprising a roof structure adapted to be installed on the reservoir to seal the same from the atmosphere, wherein said roof structure includes a gas-impermeable membrane adapted to float on top of the organic waste to raise and lower with a level of the organic waste while at the same time trapping gas generated from the decomposition of the organic waste beneath said gas-impermeable membrane.

BRIEF DESCRIPTION OF THE DRAWINGS

Having thus generally described the nature of the invention, reference will now be made to the accompanying drawings, showing by way of illustration a preferred embodiment thereof, and in which:

FIGS. 3a to 3f are schematic enlarged partial elevational views of the anaerobic digester illustrating the movement of the inner gas-impermeable membrane with the level of liquid manure contained in the reservoir;

DESCRIPTION OF THE PREFERRED EMBODIMENTS

Figure 1:
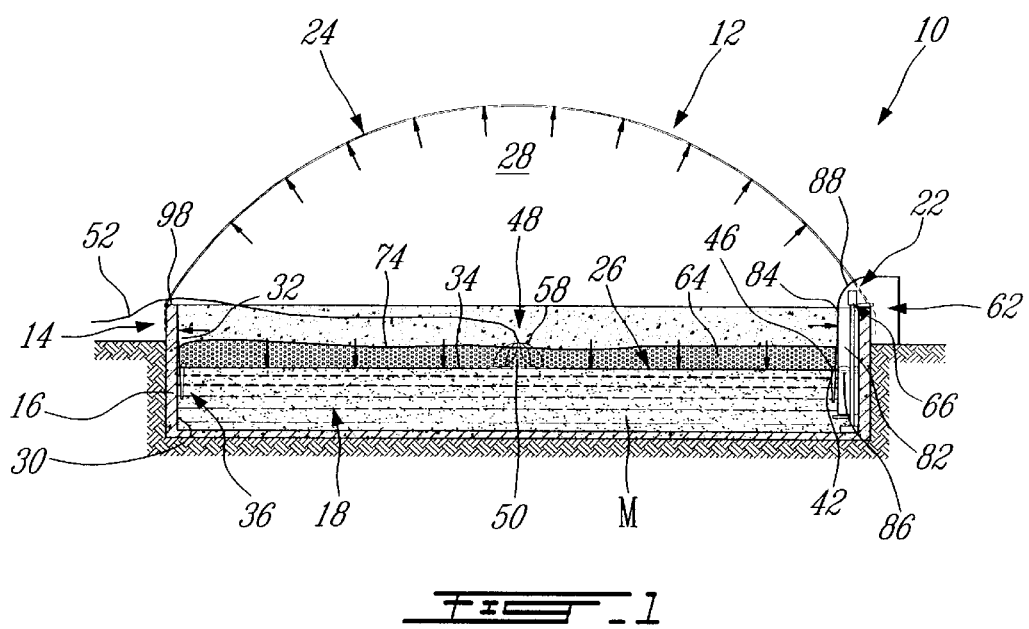
FIG. 1 is a schematic elevational cross-sectional view of a liquid manure reservoir which has been converted into an anaerobic digester by installing thereon a system in accordance with a preferred embodiment of the present invention.

FIG. 1 illustrates a system 10 for converting a variety of reservoirs into anaerobic digesters, wherein organic waste, such as liquid manure, contained in the reservoirs can be anaerobically decomposed to produce methane gas which can be collected for subsequent utilization as a combustible agent, while the manure remaining after decomposition can be used as a nutrient source.

As will be seen hereinafter, the present invention allows to stabilize, deodorize, reduce pollution potential and add value to organic waste, such as raw animal manure.

The system 10 generally comprises an inflatable roof structure 12 adapted to be sealingly installed, for instance, on a concrete cylindrical reservoir 14 to form therewith an anaerobic digester. The reservoir 14 includes a surrounding containing wall 16 defining a chamber 18 in which liquid manure M can be introduced via a feed line 20 (FIGS. 5 and 6) extending through the roof structure 12 and into the reservoir 14 at a given location along the circumference thereof. The system 10 may further comprise an optional submersible pump 22 which can be used to agitate the liquid manure M in the reservoir 14 and to withdraw the liquid manure M from the reservoir 14 without having to remove the roof structure 12 therefrom.

The inflatable roof structure 12 includes an outer liquid-impermeable membrane 24 and an inner gas-impermeable membrane 26. The outer and inner membranes 24 and 26 are adapted to be attached to the reservoir 14 to form a closed volume 28 thereover into which pressurized air can be directed to inflate the outer membrane 24 so that it forms a dome-shaped roof over the reservoir 14 to prevent precipitation, e.g. rain, from entering into the chamber 18 of the reservoir 14. The outer membrane 24 can be made of a vinyl material or any other flexible structural fabric which will resist to the elements. The inner gas-impermeable membrane 26 is preferably made of a polyethylene material.

As best seen in FIGS. 1 and 3a to 3f, the inner gas-impermeable membrane 26 extends across the chamber 18 and over the liquid manure M to seal the chamber 18 from the atmosphere, thereby allowing anaerobic conditions to be reached therein. More particularly, the inner gas-impermeable membrane 26 is sealingly attached at its peripheral edges to an upper portion of an inner surface 30 of the surrounding containing wall 16 of the reservoir 14 and extends downwardly therefrom substantially along the inner surface 30 of the surrounding containing wall 16 and then horizontally over the liquid manure M contained in the chamber 18. The inner gas-impermeable membrane 26 has a peripheral adjustable wall overlying portion 32 and a central portion 34 extending inwardly thereof and floating on top of the liquid manure M. A fold 36 is formed in the inner gas-impermeable membrane 26 about the central portion 34 thereof adjacent the inner surface 30 of the surrounding containing wall 16 of the reservoir 14 to provide a peripheral depending skirt which extends below the level of liquid manure M to allow the central portion 36 of the membrane 26 to displace vertically with the level of the manure M and to act as a barrier to prevent the biogas generated during the transformation of the liquid manure M from escaping along the inner surface 30 of the surrounding containing wall 16 of the reservoir 14. Ballast 38 (FIGS. 3a to 3f) is provided within the fold 36 to ensure that the same will remain settled in the liquid manure M. The inner gas-impermeable membrane 26 can be slightly conical to facilitate the formation of the fold 36.

As schematically illustrated in FIGS. 3a to 3f, the depth of the fold 36 will vary according to the level of liquid manure M contained in the chamber 18, and the central portion 34, which acts as a floating floor, will be allowed to raise and lower with the level of liquid manure M, while still preserving the airtightness of the chamber 18. When the level of the liquid manure M is low (FIGS. 3a and 3b), the depth of the fold 36 is small and the portion of the inner membrane 26 which is unfolded to form the wall overlying portion 26 is great. In contrast, when the level of the liquid manure M raises, the portion of the gas-impermeable membrane 26 overlying the inner surface 30 decreases and the depth of the fold 36 increases, as generally shown in FIGS. 3a to 3f.

The fold 36 defines an open pocket 40 which is filled up with a liquid 42 to prevent the pocket 40 from collapsing under the pressure exerted thereon by the liquid manure M. If the pocket 40 was left empty, the opposed inner facing sides 44a and 44b of the pocket 40 would very likely be pressed against each other, resulting in frictional forces opposing to the mobility of the central portion 34 of the inner gas-impermeable membrane 26.

Peripheral floating members 46 are provided about the central portion 34 and inwardly of the fold 36 to preserve the relative lateral position of the central portion 34 and the wall overlying portion 32 of the gas-impermeable membrane 26. The peripheral floating members 46 are attached to the inner side 44b of the pocket 40 to support the ballast 38. The combined effect of the peripheral floating members 46 and the ballast 38 will create a tension on the central portion 34 so as to maintain the latter slightly stretched at all time, which will contribute to push the biogas generated during the anaerobic transformation of the liquid manure M towards the center of the central portion 34. i.e. where the resistance is less.

Figure 2:
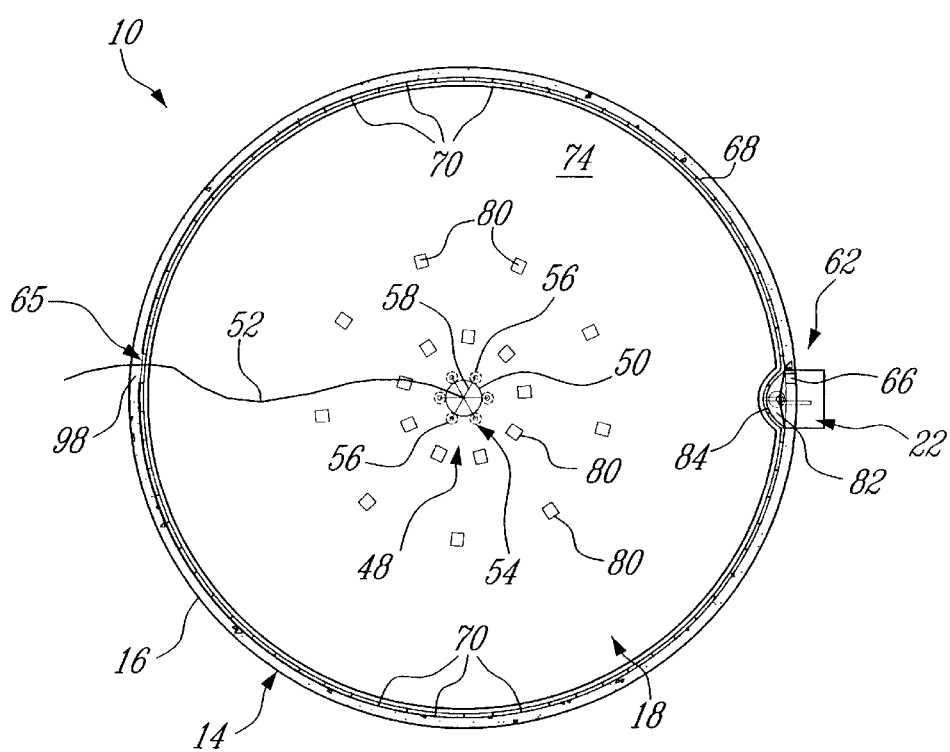
FIG. 2 is a schematic top plan view of a so formed anaerobic digester comprising an inflatable roof structure including an outer membrane and an inner gas-impermeable membrane, the outer membrane being omitted for clarity.
Figure 4:
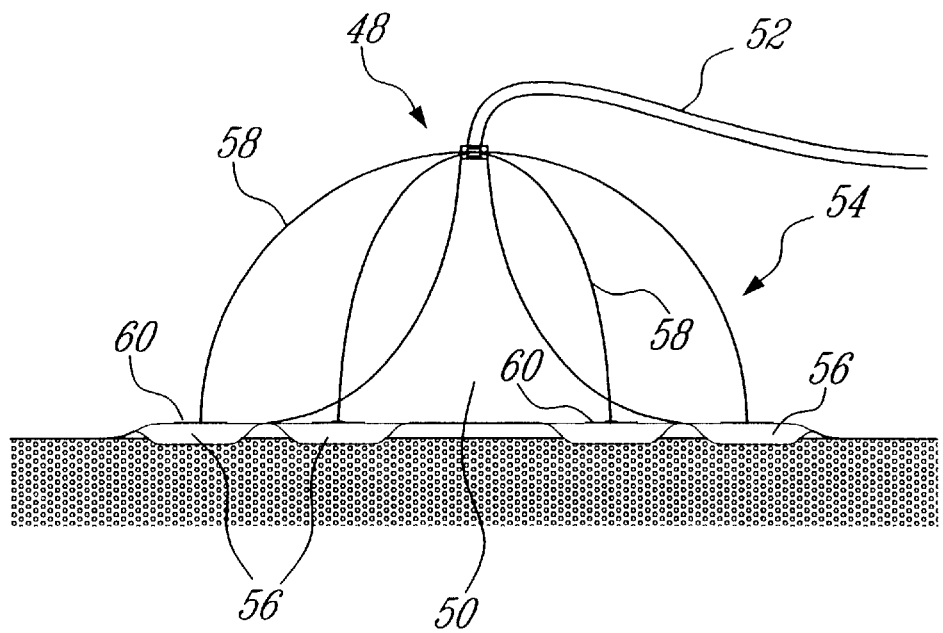
FIG. 4 is a schematic elevational view of a gas removal unit forming part of the system to remove gas entrapped beneath the inner gas-impermeable membrane.

As seen in FIGS. 1, 2 and 4, the system 10 further includes a gas removal unit 48 having a coupling sleeve 50 connected at a first end thereof in fluid flow communication to a central opening (not shown) defined through the central portion 34 of the gas-impermeable membrane 26. The coupling sleeve 50 is connected at a second opposed end thereof to a flexible hose 52 extending outwardly of the reservoir 14 to convey the methane, which is generated during the anaerobic transformation of the liquid manure M and which is entrapped beneath the gas-impermeable membrane 26, away from the chamber 18. When it is not desired to recover the generated methane, the flexible hose 52 can simply open to the ambient air, and the pressure within the closed volume 28 will cause the methane to flow through the coupling sleeve 50 and the flexible hose 52 to the ambient air. However, it is understood that the flexible hose 52 can be connected to a pump (not shown) or the like to draw the methane from the sealed chamber 18 and collect the same in a tank (not shown) for subsequent use as a combustible agent.

As best seen in FIG. 4, the coupling sleeve 50 is maintained in a vertical orientation by a support structure 54 floating on top of the inner gas-impermeable membrane 26 within the closed volume 28. The support structure 54 includes a number of floats 56 circumferentially distributed about the coupling sleeve 50. The coupling sleeve 50 is structurally connected to the floats 56 by means of flexible legs 58 extending from an upper end portion of the coupling sleeve 50 to rigid discs 60 provided on respective top surfaces of the floats 56. The legs 58 can be loosely connected to the coupling sleeve 50 and pivotally mounted to respective discs 60 to allow the support structure 54 and the coupling sleeve 50 to move relative to one another. The circumferential spaces between the floats 56 allow the gas generated (the methane) by the anaerobic transformation of the liquid manure M to flow to the mouth of the coupling sleeve 50.

Referring to FIGS. 1, 2, 8a, 8b and 9, it can be seen that the system 10 further includes an insulating foam generator 62 (FIGS. 1 and 2) adapted to be continuously or intermittently operated to produce a replaceable insulating layer of foam liquid 64 (FIG. 1) on top of the central portion of the gas-impermeable membrane so as to maintain the liquid manure M within the chamber 18 at a predetermined temperature. The thickness of the replaceable foam layer 64 can be controlled according to the requirements of each application.

The foam generator 62 includes an air pump 66 (FIGS. 1 and 2) mounted within the closed volume 28 and connected to a network of tubes 65 (FIGS. 2, 8a and 8b) comprising a main circumferential branch 68 from which depends a number of circumferentially distributed branch segments 70. The lower end of each branch segment 70 extends into the fold 36 below the level of liquid 42 contained in the pocket 40 thereof and defines an air outlet in which an air stone 72 (FIG. 8b), such as those used in aquariums, is provided to diffuse the air and, thus, promote the generation of bubbles as air is supplied into the liquid 42 through the air outlet. The liquid contained in the fold 36 can be provided in the form of a foam producing liquid, such as liquid soap. By blowing air from the pump 66 through the network of tubes 65 and into the liquid 42, bubbles will emerged from the fold 36 and eventually fill all the space between the central portion 34 of the gas-impermeable membrane 26 and a retention membrane 74 (FIGS. 1, 2, 8a and 9) extending thereabove. If there is a gradual degeneration of the so-formed foam layer 64, the liquid produced from the collapsed foam will drain back into the fold 36 for regeneration. The central portion 34 of the inner gas-impermeable membrane 26 is preferably stretched so as to define a slope from the center thereof to the fold 36 in order to ensure proper outward drainage of the liquid into the fold 36.

Figure 9:
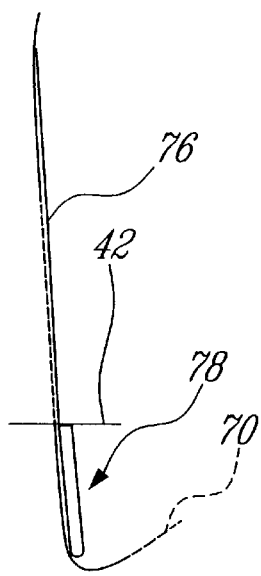
FIG. 9 is a schematic enlarged elevational view of a side wall of a retention membrane extending over the gas-impermeable membrane to retain the insulation foam material.

The retention membrane 74 has a surrounding side wall 76 (FIGS. 8a and 9) which extends into the fold 36. As shown in FIG. 9, the lower edge portion of the surrounding side wall 76 can be folded over to form a pocket 78 into which some of the liquid 42 will be entrapped, thereby offering a resistance to the withdrawal of the surrounding side wall 76 from the fold 36. The pocket 78 also acts as a barrier for breaking the foam coming into contact therewith. As shown FIG. 2, a plurality of vents 80 are defined in the retention membrane 74 for releasing the air generated from the degradation of the insulating foam while preventing escape of the liquid content thereof. Each vent 80 can consists of a patch of material which is liquidtight but permeable to gases.

As shown in FIGS. 1 and 2, the submersible pump 22 is placed in a well 82 formed by a rampart 84 and the adjacent inner surface 30 of the surrounding containing wall 16 of the reservoir 14. The wall overlying portion 32 of the inner gas-impermeable membrane 26 is deviated at this location so as to overly the rampart 84 rather than the inner surface 30. A pneumatic plug 86 is provided within the well 82 at the level of the liquid manure M to prevent gas leakage. A sealing membrane 88 extends from an upper end of the rampart 84 to the outer membrane 24 to preserve the integrity of the closed volume 28.

Figure 5:
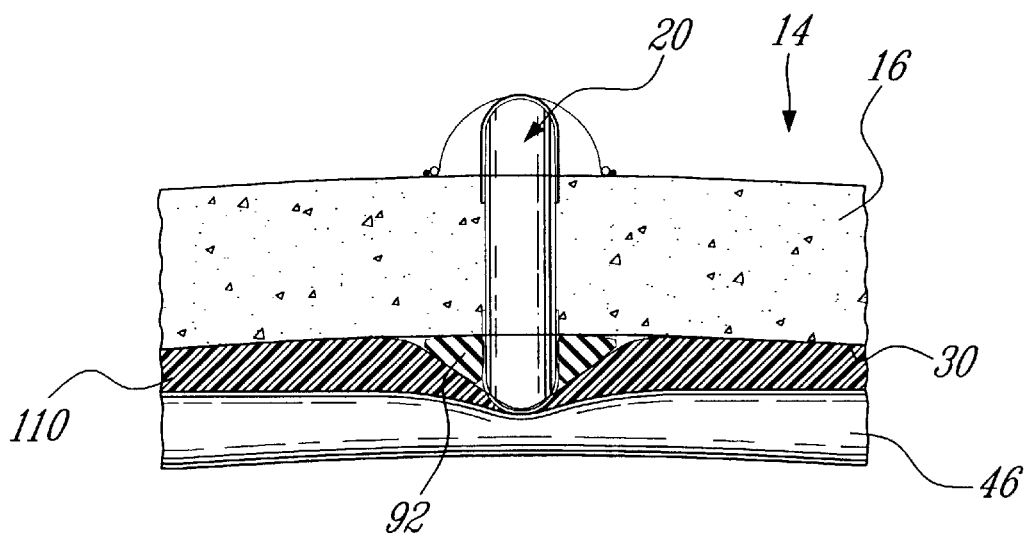
FIG. 5 is a schematic enlarged top plan view of a feed line arrangement which can be used to direct liquid manure into the reservoir beneath the inner gas-impermeable membrane.
Figure 6:
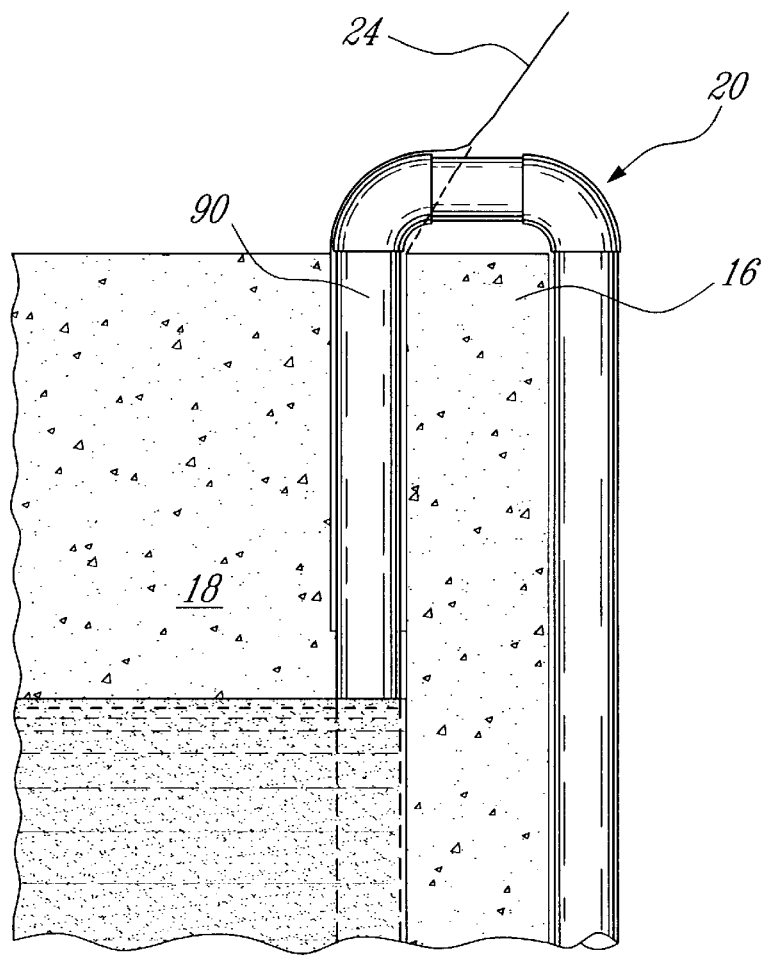
FIG. 6 is a schematic enlarged cross-sectional elevational view of the feed line arrangement of FIG. 5.

As shown in FIGS. 5 and 6, the feed line 20 includes a vertical pipe segment 90 extending downwardly into the reservoir 14 between the inner surface 30 of the surrounding containing wall 16 and the wall overlying portion 32 of the inner gas-impermeable membrane 26. A seal 92 is provided about the vertical pipe segment 90 to limit gas leakage therealong, while allowing a slight leak in order to evacuate any gas present where the wall overlying portion 32 of the inner gas-impermeable membrane 24 is deviated by the vertical pipe segment 90.

Figure 7:
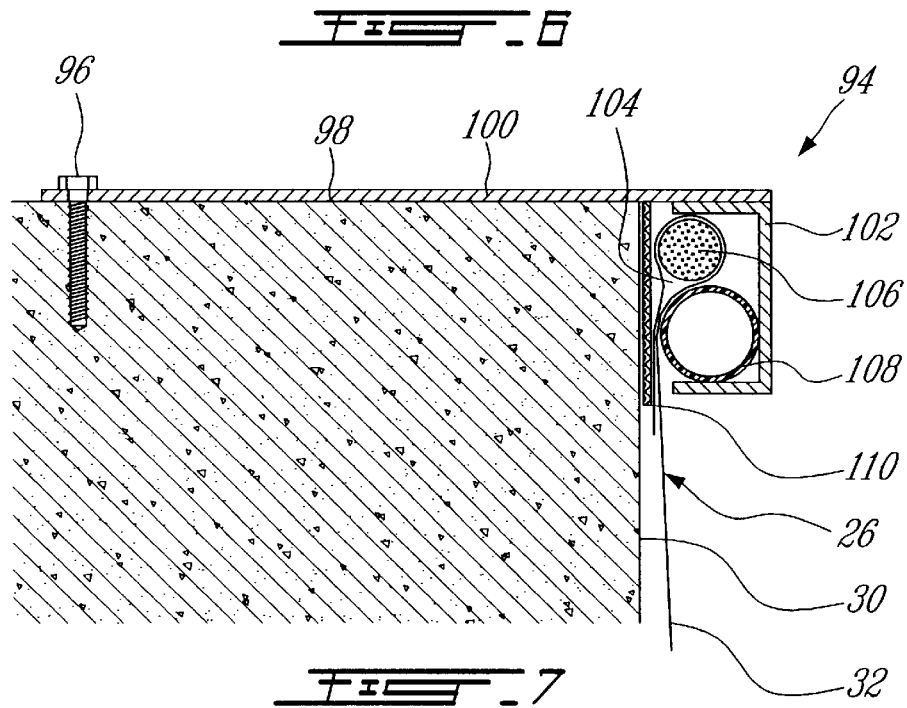
FIG. 7 is a schematic enlarged cross-sectional elevational view of a detail of the system illustrating how the gas-impermeable membrane is attached to the reservoir.
Figure 8A:
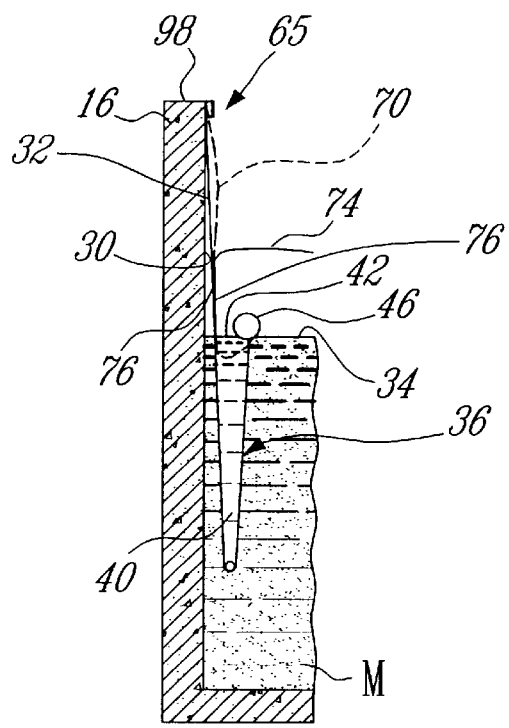
FIG. 8a is a schematic enlarged elevational view of a portion of a foam generator used for producing a layer of insulation material on top of the inner gas-impermeable membrane.
Figure 8B:
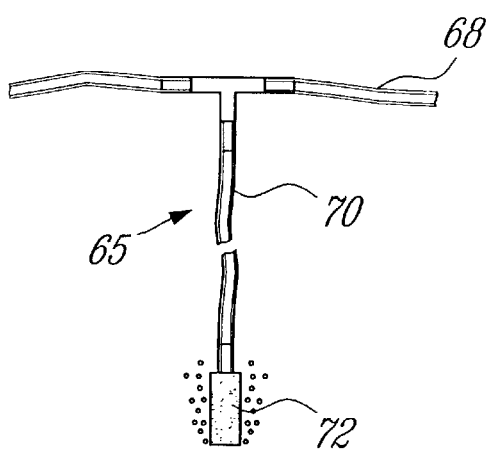
FIG. 8b is a schematic enlarged elevational view of a conduit forming part of the foam generator for directing pressurized air into a liquid reservoir defined into a peripheral portion of the inner gas-impermeable membrane.

As shown in FIG. 7, the inner gas-impermeable membrane 26 can be attached to the upper end portion of the inner surface 30 of the surrounding containing wall 16 of the reservoir 14 by means of brackets, one of which being shown at 94 in FIG. 7, secured at circumferential spaced-apart locations on a top surface 98 of the surrounding containing wall 16 of the reservoir 14 via appropriate threaded fasteners 96. Each bracket 94 includes a flat arm portion 100 extending on top of the reservoir 14 and a C-shaped channel member 102 welded to an undersurface of the flat arm portion 100 at an inner distal end thereof. The C-shaped channel member 102 is oriented so that its open side faces the inner surface 30 of the surrounding containing wall 16 of the reservoir 14 once the flat arm portion 100 has been secured on the top surface 98. The peripheral portion of the inner gas-impermeable membrane 26 is folded over so as to form a peripheral loop 104 into which a rope 106 is passed. A pipe 108 is provided within the C-shaped channel member 102 to wedge the rope 106 against the inner surface 30 of the surrounding containing wall 16 of the reservoir 14. A resilient pad 110 or the like can be inserted between the inner surface 30 of the surrounding containing wall 16 and the inner gas-impermeable membrane 26 to improve the airtightness of the arrangement.

The outer membrane 24 is preferably secured on the outer surface of the surrounding containing wall 16 by means of pipe (not shown) wedging a rope (not shown), which is passed in a loop (not shown) formed at the periphery of the outer membrane 24, against the outer surface of the surrounding containing wall 16, as described hereinbefore with respect to the inner gas-impermeable membrane 26.

Although the roof structure 12 has been described as being inflatable, it is also contemplated to replace the outer membrane 24 by a rigid cover (not shown). It is also understood that the present invention is not limited to be used in conjunction with a liquid manure reservoir but could be used with a large variety of organic waste reservoirs as well.

What is claimed is:

1. A system for converting a reservoir into an anaerobic digester in which organic waste contained in the reservoir can be at least partly anaerobically decomposed, wherein the reservoir is of the type having a surrounding containing wall, the system comprising a roof structure adapted to be installed on the reservoir to seal the reservoir from the atmosphere, said roof structure including a gas-impermeable membrane adapted to extend over the organic waste contained in the reservoir for trapping, beneath said gas-impermeable membrane, gas generated during decomposition of the organic waste in the reservoir, said gas-impermeable membrane having a peripheral depending skirt adapted to extend downwardly and inwardly of an inner surface of the surrounding containing wall of the reservoir below a level of organic waste to prevent the gas from escaping along the inner surface of the reservoir, wherein said gas-impermeable membrane is adapted to float on top of the organic waste to raise and lower with the level of organic waste in the reservoir.

2. A system as defined in claim 1, wherein said gas-impermeable membrane is adapted to be sealingly attached to the inner surface of the surrounding containing wall of the reservoir.

3. A system as defined in claim 1, wherein said gas-impermeable membrane is adapted to be attached to the reservoir with a wall overlying portion of said gas-impermeable membrane extending downwardly along the inner surface of the surrounding containing wall of the reservoir and a central portion of said gas-impermeable membrane floating on top of the organic waste contained in the reservoir, a fold being provided in said gas-impermeable membrane about said central portion to form said downwardly depending skirt and allow said central portion to raise and lower with the level of organic waste, while preventing gas from escaping along the inner surface of the surrounding containing wall of the reservoir.

4. A system as defined in claim 3, wherein a floating structure is provided at a periphery of said central portion of said gas-impermeable membrane to preserve a relative position of said wall overlying portion and said central portion.

5. A system as defined in claim 3, wherein said fold defines a pocket having an open top end, said pocket being adapted to vary in depth according to the level of organic waste in the reservoir.

6. A system as defined in claim 5, wherein liquid is provided within said pocket to prevent the same from collapsing under the pressure exerted thereon by the organic waste.

7. A system as defined in claim 5, wherein a ballast is provided within said pocket to ensure that said fold remains settled in the organic waste.

8. A system as defined in claim 1, wherein said roof structure further includes an external cover extending over said gas-impermeable membrane to prevent precipitation from entering into the reservoir.

9. A system as defined in claim 8, wherein said external cover comprises a liquid-impermeable membrane adapted to be installed on the reservoir to form with said gas-impermeable membrane an enclosed space in which a gas is provided under pressure such that said liquid-impermeable membrane assumes a dome-shaped configuration and said gas-impermeable membrane is pressed against the inner surface of the surrounding containing wall of the reservoir and the organic waste contained therein.

10. A system as defined in claim 1, wherein a layer of insulating material is provided on top of said gas-impermeable membrane to maintain a desired temperature in the reservoir.

11. Air A system as defined in claim 10, wherein said layer of insulating material includes a replaceable insulating foam which is produced by a foam generator and directed in a cavity defined between said gas-impermeable membrane and a retention membrane extending thereabove.

12. A system as defined in claim 11, wherein a plurality of vents are defined in said retention membrane for releasing gases generated from a degradation of said insulating foam while preventing a liquid content of the insulating foam from escaping therethrough.

13. A system as defined in claim 11, wherein a fold is defined in said gas-impermeable membrane adjacent the inner surface of the surrounding containing wall of the reservoir, said fold forming said downwardly depending skirt, and wherein said gas-impermeable membrane is sloped to cause liquid, produced from collapsed insulating foam to drain into said fold for subsequent regeneration.

14. A system as defined in claim 13, wherein a foam destroying barrier is provided at an entry end of said fold.

15. A system as defined in claim 1, further including a gas removal unit for removing the gas trapped beneath said gas-impermeable membrane, said gas removal unit including a conduit connected to a hole defined in said gas-impermeable membrane.

16. A system as defined in claim 15, wherein said roof structure includes an inflatable roof, said gas-impermeable membrane forming part of said inflatable roof such as to cause the gas generated during decomposition of the organic waste in the reservoir to flow through said conduit under a pressure exerted by the inflatable roof.

17. A system as defined in claim 15, wherein said conduit includes a coupling sleeve and a gas line in fluid communication with said coupling sleeve, said coupling sleeve being sealingly connected to said hole in said gas-impermeable membrane and supported thereon by a floating structure.

18. A system as defined in claim 17, wherein said hole is defined in a central area of said gas-impermeable membrane.

19. A system as defined in claim 17, wherein said floating structure extends about said coupling sleeve and is discontinuous to allow the gas to flow to the coupling sleeve.

20. A system as defined in claim 1, further including a submersible pump beneath said gas-impermeable membrane for mixing the organic waste and allowing the same to be discharged from the reservoir without having to remove said roof structure.

21. An anaerobic digester comprising a surrounding wall forming a digester vessel for containing an organic waste material, a roof structure for sealing said digester vessel from the atmosphere, said roof structure comprising a gas-impermeable membrane adapted to extend over the organic waste contained in said digester vessel for trapping, beneath said gas-impermeable membrane, gas generated from a decomposition of the organic waste, said gas-impermeable membrane having a peripheral depending skirt adapted to extend downwardly and inwardly of an inner surface of said surrounding wall of said digester vessel below a level of organic waste to prevent the gas from escaping along said inner surface, wherein said gas-impermeable membrane is adapted to float-on top of the organic waste to raise and lower with the level of organic waste in said digester vessel.

22. An anaerobic digester as defined in claim 21, wherein said gas-impermeable membrane is adapted to be attached at a peripheral portion thereof to an upper portion of said digester vessel with a wall overlying portion of said gas-impermeable membrane extending downwardly along said inner surface of said surrounding wall of said digester vessel and a central portion of said gas-impermeable membrane floating on top of the organic waste contained in said digester vessel, a fold being provided in said gas-impermeable membrane about said central portion thereof to form said downwardly depending skirt and allow said central portion to raise and lower with the level of organic waste, while preventing gas from escaping along said inner surface of said surrounding wall of said digester vessel.

23. An anaerobic digester as defined in claim 22, wherein a floating structure is provided at a periphery of said central portion of said gas-impermeable membrane to preserve a relative position of said wall overlying portion and said central portion.

24. An anaerobic digester as defined in claim 22, wherein said fold defines a pocket having an open top end, said pocket being adapted to vary in depth according to the level of organic waste in said digester vessel.

25. An anaerobic digester as defined in claim 24, wherein liquid is provided within said pocket to prevent the same from collapsing under the pressure exerted thereon by the organic waste.

26. An anaerobic digester as defined in claim 24, wherein a ballast is provided within said pocket to ensure that said fold remains settled in the organic waste.

27. An anaerobic digester as defined in claim 22, further including an external cover extending over said gas-impermeable membrane to prevent precipitation from entering into said digester vessel.

28. An anaerobic digester as defined in claim 27, wherein said external cover comprises a liquid-impermeable membrane adapted to be installed on said digester vessel to form with said gas-impermeable membrane an enclosed space in which a gas is provided under pressure such that said liquid-impermeable membrane assumes a dome-shaped configuration and said gas-impermeable membrane is pressed against said inner surface of said surrounding wall of said digester vessel and the organic waste contained therein.

29. An anaerobic digester as defined in claim 21, wherein a replaceable layer of insulating material is provided on top of said gas-impermeable membrane to maintain a desired temperature in said digester vessel.

30. A system for converting an existing reservoir containing an organic waste into an anaerobic digester, comprising an inflatable roof structure adapted to be installed on the existing reservoir for allowing anaerobic conditions to be reached therein, and a gas removal unit for removing gas captured beneath said inflatable roof structure from the existing reservoir, wherein said inflatable roof structure includes an external membrane and an internal membrane defining an enclosed space, and wherein a replaceable insulating foam layer is provided within said enclosed space on top of said internal membrane.

31. A system as defined in claim 30, wherein said gas removal unit includes a conduit for conducting the gas captured beneath said inflatable roof structure away from the existing reservoir under a pressure exerted by said inflatable roof structure on the organic waste contained in the reservoir.

32. A system for converting a reservoir into an anaerobic digester in which organic waste contained in the reservoir can be at least partly anaerobically decomposed, wherein the reservoir is of the type having a surrounding containing wall, the system comprising a roof structure adapted to be installed on the reservoir to seal the reservoir from the atmosphere, said roof structure including a gas-impermeable membrane adapted to extend over the organic waste contained in the reservoir for trapping, beneath said gas-impermeable membrane, gas generated during decomposition of the organic waste in the reservoir, said gas-impermeable membrane having a peripheral depending skirt adapted to extend downwardly and inwardly of an inner surface of the surrounding containing wall of the reservoir below a level of organic waste to prevent the gas from escaping along the inner surface of the reservoir, wherein said gas-impermeable membrane is adapted to be attached to the reservoir with a wall overlying portion of said gas-impermeable membrane extending downwardly along the inner surface of the surrounding containing wall of the reservoir and a central portion of said gas-impermeable membrane floating on top of the organic waste contained in the reservoir, a fold being provided in said gas-impermeable membrane about said central portion to form said downwardly depending skirt and allow said central portion to raise and lower with the level of organic waste, while preventing gas from escaping along the inner surface of the surrounding containing wall of the reservoir.

33. A system as defined in claim 32, wherein said fold defines a pocket having an open top end, said pocket being adapted to vary in depth according to the level of organic waste in the reservoir.

34. A system as defined in claim 33, wherein liquid is provided within said pocket to prevent the same from collapsing under the pressure exerted thereon by the organic waste.

35. A system for converting a reservoir into an anaerobic digester in which organic waste contained in the reservoir can be at least partly anaerobically decomposed, wherein the reservoir is of the type having a surrounding containing wall, the system comprising a roof structure adapted to be installed on the reservoir to seal the reservoir from the atmosphere, said roof structure including a gas-impermeable membrane adapted to extend over the organic waste contained in the reservoir for trapping, beneath said gas-impermeable membrane, gas generated during decomposition of the organic waste in the reservoir, said gas-impermeable membrane having a peripheral depending skirt adapted to extend downwardly and inwardly of an inner surface of the surrounding containing wall of the reservoir below a level of organic waste to prevent the gas from escaping along the inner surface of the reservoir, wherein a layer of insulating material is provided on top of said gas-impermeable membrane to maintain a desired temperature in the reservoir.

36. A system as defined in claim 35, wherein said layer of insulating material includes a replaceable insulating foam which is produced by a foam generator and directed in a cavity defined between said gas-impermeable membrane and a retention membrane extending thereabove.

37. A system as defined in claim 36, wherein a fold is defined in said gas-impermeable membrane adjacent the inner surface of the surrounding containing wall of the reservoir, said fold forming said downwardly depending skirt, and wherein said gas-impermeable membrane is sloped to cause liquid produced from collapsed insulating foam to drain to said fold for subsequent regeneration.

38. A system for converting a reservoir into an anaerobic digester in which organic waste contained in the reservoir can be at least partly anaerobically decomposed, wherein the reservoir is of the type having a surrounding containing wall, the system comprising a roof structure adapted to be installed on the reservoir to seal the reservoir from the atmosphere, said roof structure including a gas-impermeable membrane adapted to extend over the organic waste contained in the reservoir for trapping, beneath said gas-impermeable membrane, gas generated during decomposition of the organic waste in the reservoir, said gas-impermeable membrane having a peripheral depending skirt adapted to extend downwardly and inwardly of an inner surface of the surrounding containing wall of the reservoir below a level of organic waste to prevent the gas from escaping along the inner surface of the reservoir, further including a submersible pump beneath said gas-impermeable membrane for mixing the organic waste and allowing the same to be discharged from the reservoir without having to remove said roof structure.

39. An anaerobic digester comprising a surrounding wall forming a digester vessel for containing an organic waste material, a roof structure for sealing said digester vessel from the atmosphere, said roof structure comprising a gas-impermeable membrane adapted to extend over the organic waste contained in said digester vessel for trapping, beneath said gas-impermeable membrane, gas generated from a decomposition of the organic waste, said gas-impermeable membrane having a peripheral depending skirt adapted to extend downwardly and inwardly of an inner surface of said surrounding wall of said digester vessel below a level of organic waste to prevent the gas from escaping along said inner surface, wherein said gas-impermeable membrane is adapted to be attached at a peripheral portion thereof to an upper portion of said digester vessel with a wall overlying portion of said gas-impermeable membrane extending downwardly along said inner surface of said surrounding wall of said digester vessel and a central portion of said gas-impermeable membrane floating on top of the organic waste contained in said digester vessel, a fold being provided in said gas-impermeable membrane about said central portion thereof to form said downwardly depending skirt and allow said central portion to raise and lower with the level of organic waste, while preventing gas from escaping along said inner surface of said surrounding wall of said digester vessel.

40. An anaerobic digester as defined in claim 39, wherein said fold defines a pocket having an open top end, said pocket being adapted to vary in depth according to the level of organic waste in said digester vessel.

41. An anaerobic digester as defined in claim 40, wherein liquid is provided within said pocket to prevent the same from collapsing under the pressure exerted thereon by the organic waste.

42. An anaerobic digester comprising a surrounding wall forming a digester vessel for containing an organic waste material, a roof structure for sealing said digester vessel from the atmosphere, said roof structure comprising a gas-impermeable membrane adapted to extend over the organic waste contained in said digester vessel for trapping, beneath said gas-impermeable membrane, gas generated from a decomposition of the organic waste, said gas-impermeable membrane having a peripheral depending skirt adapted to extend downwardly and inwardly of an inner surface of said surrounding wall of said digester vessel below a level of organic waste to prevent the gas from escaping along said inner surface, wherein a replaceable layer of insulating material is provided on top of said gas-impermeable membrane to maintain a desired temperature in said digester vessel.

* * * * *